United States Patent [19]
Pike et al.

[11] Patent Number: 5,695,506
[45] Date of Patent: Dec. 9, 1997

[54] CATHETER DEVICE WITH A FLEXIBLE HOUSING

[75] Inventors: Kelly Pike, Halfmoon Bay; David Hancock, San Francisco; Scott Argus, E. Palo Alto; Andrew Chiang, Fremont, all of Calif.

[73] Assignee: Devices for Vascular Intervention, Redwood City, Calif.

[21] Appl. No.: 596,030

[22] Filed: Feb. 6, 1996

[51] Int. Cl.⁶ ................................................. A61B 17/22
[52] U.S. Cl. ............................ 606/159; 606/167; 604/22
[58] Field of Search .................... 606/159, 167, 606/170, 171, 180; 604/22; 128/750–755

[56] References Cited

U.S. PATENT DOCUMENTS

| | | | |
|---|---|---|---|
| 4,781,186 | 11/1988 | Simpson et al. | 606/159 |
| 4,979,951 | 12/1990 | Simpson | 606/159 |
| 5,024,234 | 6/1991 | Leary et al. | 128/662.06 |
| 5,226,909 | 7/1993 | Evans et al. | 606/159 |
| 5,269,793 | 12/1993 | Simpson | 606/159 |
| 5,312,425 | 5/1994 | Evans et al. | 606/159 |
| 5,403,334 | 4/1995 | Evans et al. | 606/159 |
| 5,514,115 | 5/1996 | Frantzen et al. | 606/159 |

*Primary Examiner*—Michael Buiz
*Assistant Examiner*—Patrick W. Rasche
*Attorney, Agent, or Firm*—Peninsula IP Group; Douglas A. Chaikin

[57] ABSTRACT

Disclosed herein is a catheter device for use in a biological conduit. The catheter device has a catheter body with a housing and a torque cable lumen, a torque cable, a work element, and a connector. The housing is flexible. The torque cable extends through the catheter body to the housing via the torque cable lumen and is capable of rotation and translation with respect to the catheter body. The work element is slidably positioned in the housing. The housing has an interior which guides the work element in response to rotation and translation of the torque cable. The connector attaches the work element to the torque cable. The connector is flexible to facilitate flexion between the work element and the torque cable when the housing flexes.

3 Claims, 9 Drawing Sheets

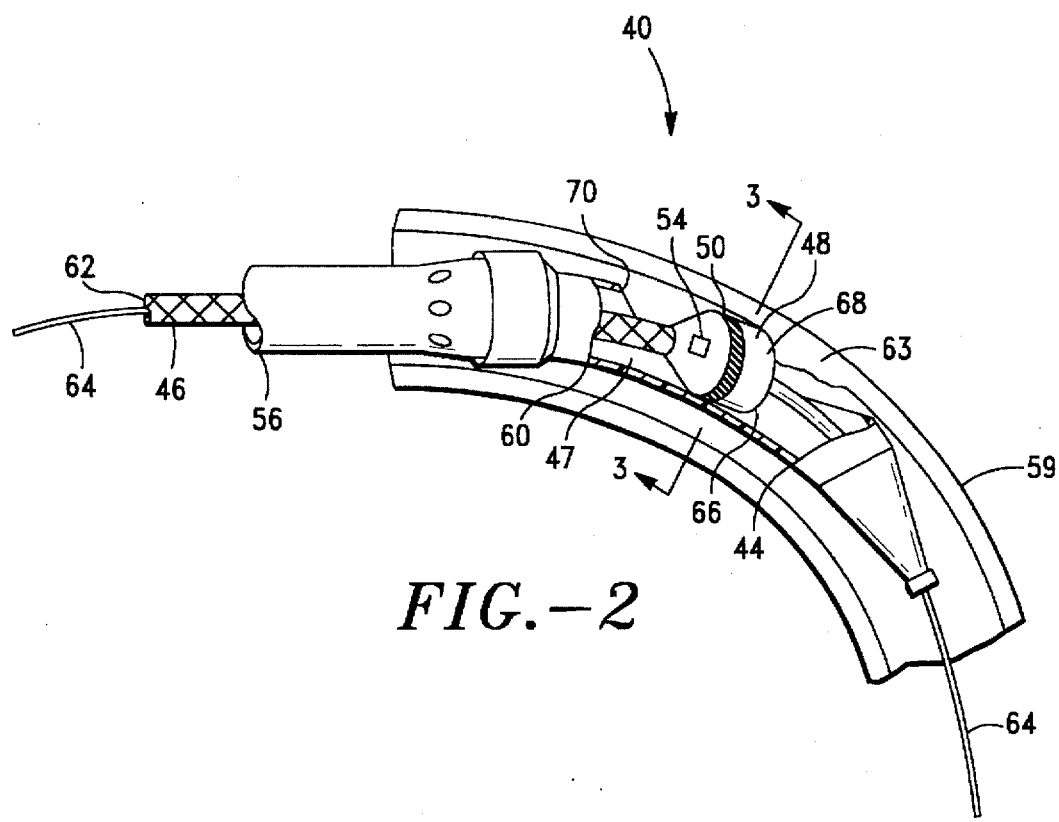
FIG.-2
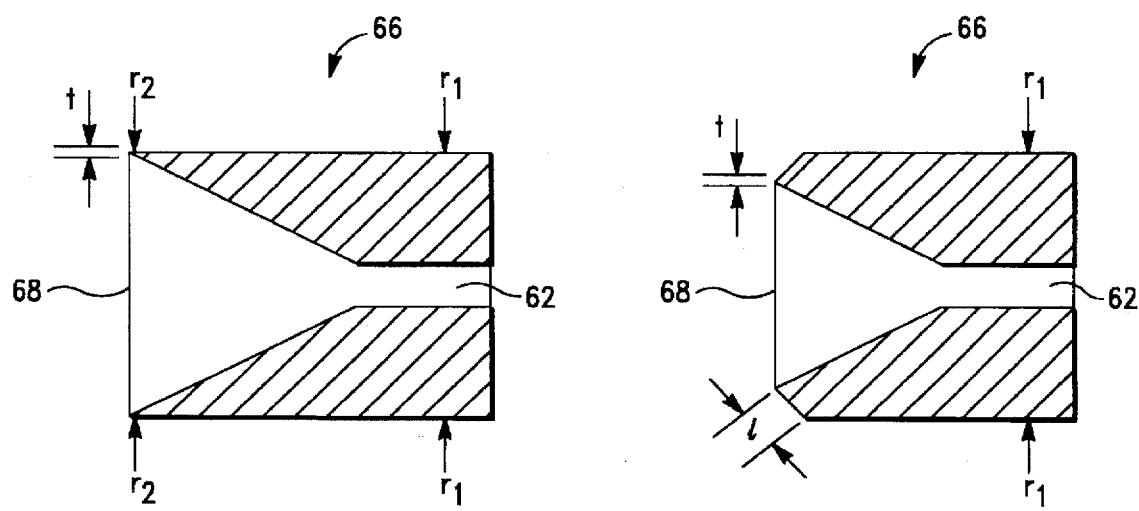
FIG.-3
FIG.-4

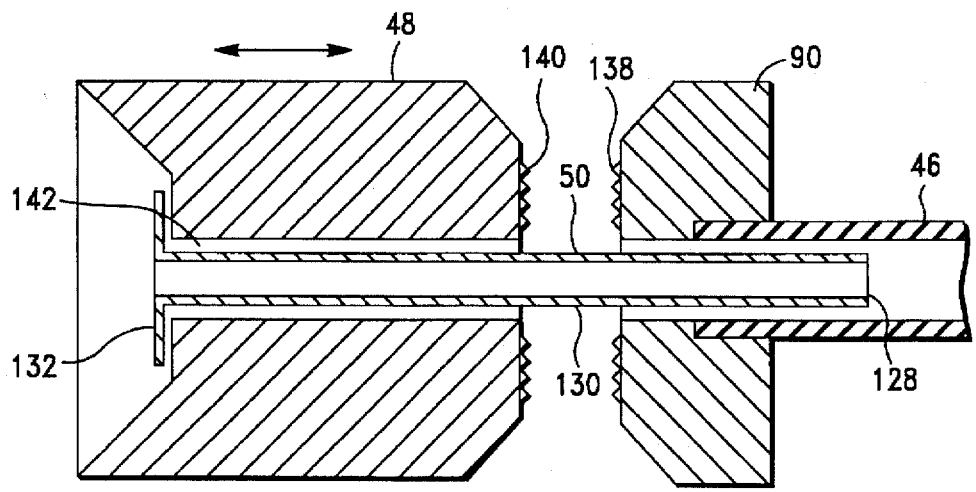
FIG.—35
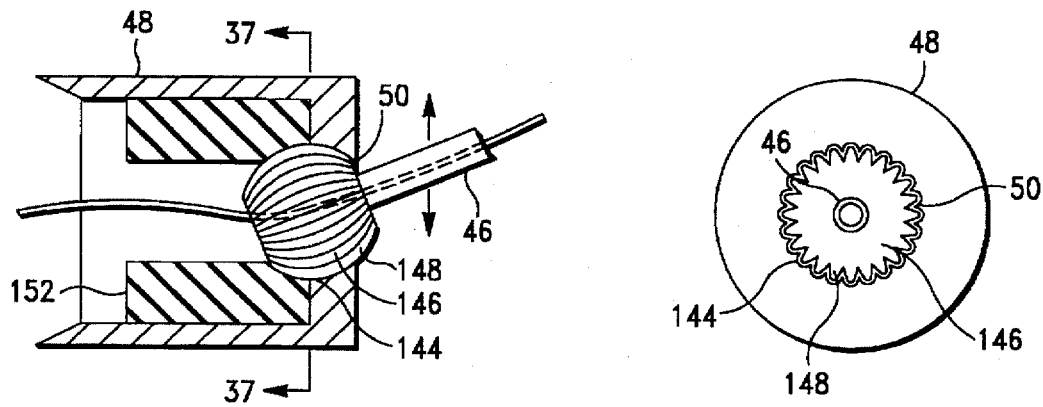
FIG.—36  FIG.—37
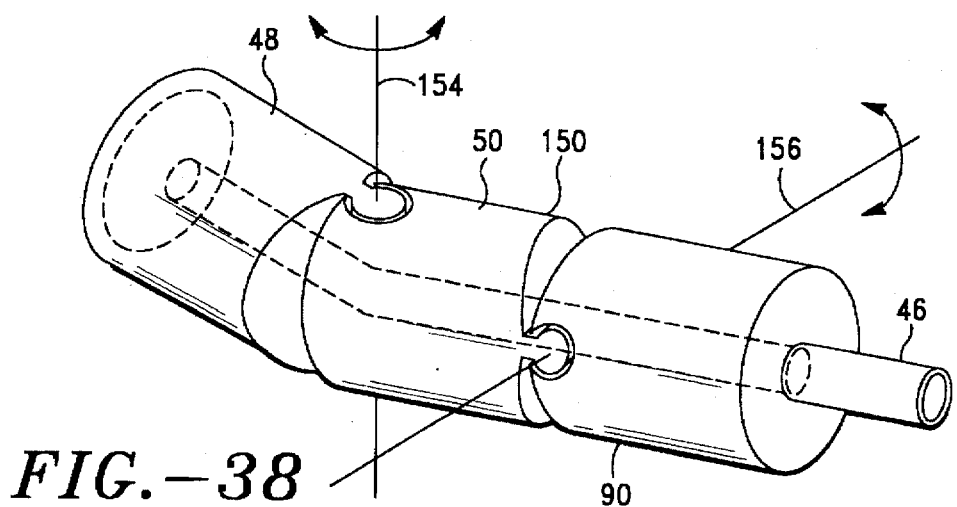
FIG.—38

CATHETER DEVICE WITH A FLEXIBLE HOUSING

RELATED PATENTS AND PATENT APPLICATIONS

This invention relates in subject matter to commonly assigned U.S. patent application Ser. No. 08/357,999 attorney docket number DEVI1476; U.S. patent application Ser. No. 08/224,169, U.S. Pat. No. 5,624,457, issue date Apr. 29, 1997 to Farley, et al.; and U.S. Pat. Nos. 4,781,186 and 5,312,425. The disclosure of each related patent and patent application is incorporated herein by reference.

BACKGROUND OF THE INVENTION

1. Field of the Invention

This invention relates to catheters which are insertable into a biological conduit. More particularly, this invention relates to atherectomy catheters having flexible housings.

2. Previous Art

Atherosclerosis is a disease characterized by the deposition of biological tissues such as atheroma or plaque, and other material, on the interior walls of blood vessels. Such deposits are generally known as stenotic material. Stenotic material can include soft tractable material, or hardened material such as calcification. Stenotic material can be deposited throughout the vasculature and is commonly found in peripheral blood vessels that feed the arms and legs and in coronary blood vessels that feed the heart, for example. Blood flow in these blood vessels is restricted when the stenotic material accumulates in localized regions. Such localized regions become occluded. Restricted blood flow, in the coronary artery for example, can cause severe health problems including heart attacks and strokes.

Numerous ways of restoring blood flow have been proposed. Balloon angioplasty, for example, uses a balloon-tipped catheter to dilate the occluded region of the blood vessel. Laser angioplasty uses a laser to direct energy to ablate atheroma portions. Atherectomy uses a catheter with a distal end and a housing attached at the distal end. A cutter moveably attaches within the housing to sever and remove stenosis from an occluded portion of a blood vessel.

During an atherectomy procedure, a guidewire is first inserted into the vasculature of a patient via the femoral artery, for example. The guidewire advances through the vasculature to the stenosed region of an occluded blood vessel. The catheter slides along the guidewire until the distal end of the atherectomy catheter positions adjacent the stenosis.

The atherectomy catheter has a work element such as a cutting blade which reciprocally advances past an opening at the distal end of the atherectomy catheter. Stenotic material from the blood vessel extends from the blood vessel wall. The opening invaginates portions of the stenotic material. The cutting blade advances. Each time the blade advances, the blade cuts a small portion of the stenotic material. Typically, such cutting blades are arcuate in shape. The cutting blade rotates (or rotationally oscillates) as the blade advances to effectuate cutting.

Although such atherectomy catheters have enjoyed widespread success in both peripheral and coronary applications, certain design limitations persist. In relatively small diameter blood vessels (e.g. those having a diameter of less than 1 cm) such as the coronary arteries, very tight vascular bends are encountered. Atherectomy catheters having rigid housings at their distal ends have difficulty inserting past such tight vascular bends. To ease insertion of atherectomy catheters, catheters having flexible housings have been developed. Catheters with flexible housings are disclosed in U.S. Pat. Nos. 4,781,186; 5,226,909; and 5,312,425 the disclosures of which are incorporated herein by reference.

Flexible housings also have certain limitations. When flexed, a flexible cutter housing may interfere with the operation of an enclosed cutter. When the housing flexes, alignment between the cutter and the housing can be disturbed and interference between the cutter and the housing can more easily result. In particular, bending and flexing of a flexible housing may inhibit axial advancement of the cutter within the housing. Housing interference can also slow rotation of the cutter and limit cutting effectiveness. Such interference can dull the cutter and deform the housing.

Attempts to overcome the limitations and difficulties associated with flexible housings has resulting in the development of various work element guiding structures. An example of a guiding structure is described in commonly assigned U.S. Pat. No. 5,624,457, issue date Apr. 29, 1997, to Farley, et al. (Attorney Docket No. DEVI1467), the disclosure of which is incorporated herein by reference. A saddle attaches to a work element to retain the work element within the housing when the housing flexes.

A catheter with a flexible housing is described in commonly assigned U.S. patent application Ser. No. 08/357,999, filed Dec. 16, 1994 (Attorney Docket No. DEVI 1476), the disclosure of which is incorporated by reference. An axial guiding structure attaches to the work element to retain the work element within the housing when the housing flexes.

Housings having guiding structures are difficult to manufacture. The small size of many catheters, work elements (e.g. cutters) and guiding structures complicates fabrication and assembly. Improved intravascular catheters are desired. In particular, it is desirable to provide a catheter device which is easy to manufacture. Additionally, it is desirable to have a catheter device with a flexible housing and a work element wherein the work element does not significantly interfere with the flexible housing when the flexible housing bends. It is desirable to provide a way of minimizing interference between a moveable work element and the flexible housing.

SUMMARY AND OBJECTS OF THE INVENTION

The various objects of the invention which are presented and which will become apparent below are provided by way of example only and are not intended to limit the scope of the present invention. The present invention is to be limited in scope only by the appended Claims.

It is an object of the present invention to provide a catheter having a flexible housing with a work element which is capable of operation when the housing flexes.

It is an object of the present invention to provide a catheter housing having a rotatable work element which does not dull or lose cutting effectiveness through interference with the housing.

In accordance with the above objects and those that will be mentioned and will become apparent below, a catheter device insertable into a biological conduit, comprises:

a catheter body having a proximal end and a distal end, the catheter body defining a torque cable lumen extending between the proximal end and the distal end;

a housing connected to the distal end of the catheter body, the housing being flexible and defining an opening;

a torque cable extending between the proximal end and the distal end of the catheter body through the torque cable lumen, the torque cable being capable of sliding with respect to the torque cable lumen;

a work element slidably disposed within the housing; and a connector interconnecting the work element and the torque cable, the connector being flexible and including a flex tube, the flex tube having multiple circumferential slots to facilitate flexion of the connector, the work element being formed unitary with the connector, whereby when the housing flexes and the torque cable slides the work element, the connector flexes and the housing guides the work element within the housing.

In an embodiment of the present invention, the housing includes a flex tube with multiple circumferential slots to facilitate flexion of the housing.

In another embodiment, the work element is a cutter having an arcuate cutting edge for removing biological tissue.

In another embodiment, the cutter is beveled to facilitate sliding of the work element in the housing.

In another embodiment, the torque cable, the connector and the work element define portions of a guidewire lumen. The catheter device includes a guidewire, the guidewire extends through the guidewire lumen of the torque cable, the connector and the work element.

In another embodiment, the connector includes a flex tube. The flex tube has multiple circumferential slots to facilitate flexion of the connector.

In another embodiment, the work element is formed integral with the connector. In a variation of this embodiment, the connector includes a flex tube with two ends. The work element has an arcuate cutting edge. One end of the flex tube defines the arcuate cutting edge and the other end attaches to the torque cable.

In another embodiment, the connector includes a helical spring to facilitate flexion of the connector. The helical spring has two ends. One end of the spring attaches to the work element. The other end of the spring attaches to the torque cable. In a variation of this embodiment, the two ends of the helical spring are soldered to the torque cable and to the work element respectively.

In another embodiment, the helical spring is fabricated from wire having a diameter within the range of 0.012 inches to 0.017 inches.

In another embodiment, the helical spring has an inside diameter of about 0.037 inches and an outside diameter of less than 0.073 inches.

In another embodiment, the connector includes a duplex style spring. In a variation of this embodiment, the duplex type spring has a helical spring with a rectangular cross-section. In another variation of this embodiment, the duplex style spring has an externally wound helical spring and an internally wound helical spring. The internally wound spring opposes the externally wound spring to provide axial and torsional rigidity to the connector.

In another embodiment, the torque cable has a wall thickness, the connector has a wall thickness, and the wall thickness of the connector is relatively less than the wall thickness of the torque cable to permit the connector to flex more than the torque cable.

In another embodiment, the connector includes a resilient member having two ends. One end of the resilient member attaches to the work element, the other end attaches to the torque cable.

In another embodiment, the torque cable is a composite, being fabricated from a fiber reinforcement and a matrix, the fiber reinforcement includes braided metal, the matrix includes thermoset urethane, the connector is a composite fabricated from braided metal and thermoset urethane and having proportionately less thermoset urethane than the torque cable.

In another embodiment, the connector includes a bushing and a resilient member, the bushing attaches to the torque cable, the resilient member attaches to the work element and to the bushing.

In another embodiment, the connector includes a universal joint, the universal joint attaches the work element to the torque cable.

In another embodiment, the connector has a bushing, a resilient member and locking sleeve. The locking sleeve circumscribes the work element and the bushing to transmit torque and axial forces from the bushing to the work element.

In another embodiment, the connector includes a bushing and an internal sleeve with a proximal end and a distal end. The bushing has a clutch plate surface and the work element has a clutch plate surface. The clutch plate surfaces of the work element and the bushing engage to transmit torque between the bushing and the work element. The internal sleeve flexes to facilitate flexion of the work element with respect to the torque cable.

In another embodiment, the connector includes a bushing and a rigid internal sleeve. The rigid internal sleeve slidably holds the work element.

In another embodiment, the connector has a pinion with arcuate gear teeth. The work element has a geared portion. The arcuate gear teeth of the pinion mesh with the geared portion at a variable angle to transmit torque from the torque cable to the work element.

It is an advantage of the present invention to provide a catheter device having a flexible housing which guides a work element when the housing flexes.

It is a further advantage to provide a catheter device having a flexible housing and a work element which flexibly attaches to a torque cable.

It is a further advantage to provide a catheter housing having a rotatable work element which maintains cutting effectiveness.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 is a view of the distal end of the catheter device of FIG. 1 inserted into a biological conduit.

FIGS. 3 and 4 are cross-sectional views of embodiments of the work element of FIG. 2 as seen along the line 3—3.

FIG. 35 is a cross-sectional view of a connector in accordance with the present invention.

FIG. 36 is a cross-sectional view of a connector in accordance with the present invention.

FIG. 37 is a cross-sectional view of the connector of FIG. 36 as seen along the line 37—37 in the direction of the arrows.

FIG. 38 is a perspective view of a connector in accordance with the present invention.

DETAILED DESCRIPTION OF THE INVENTION

Figure 1:
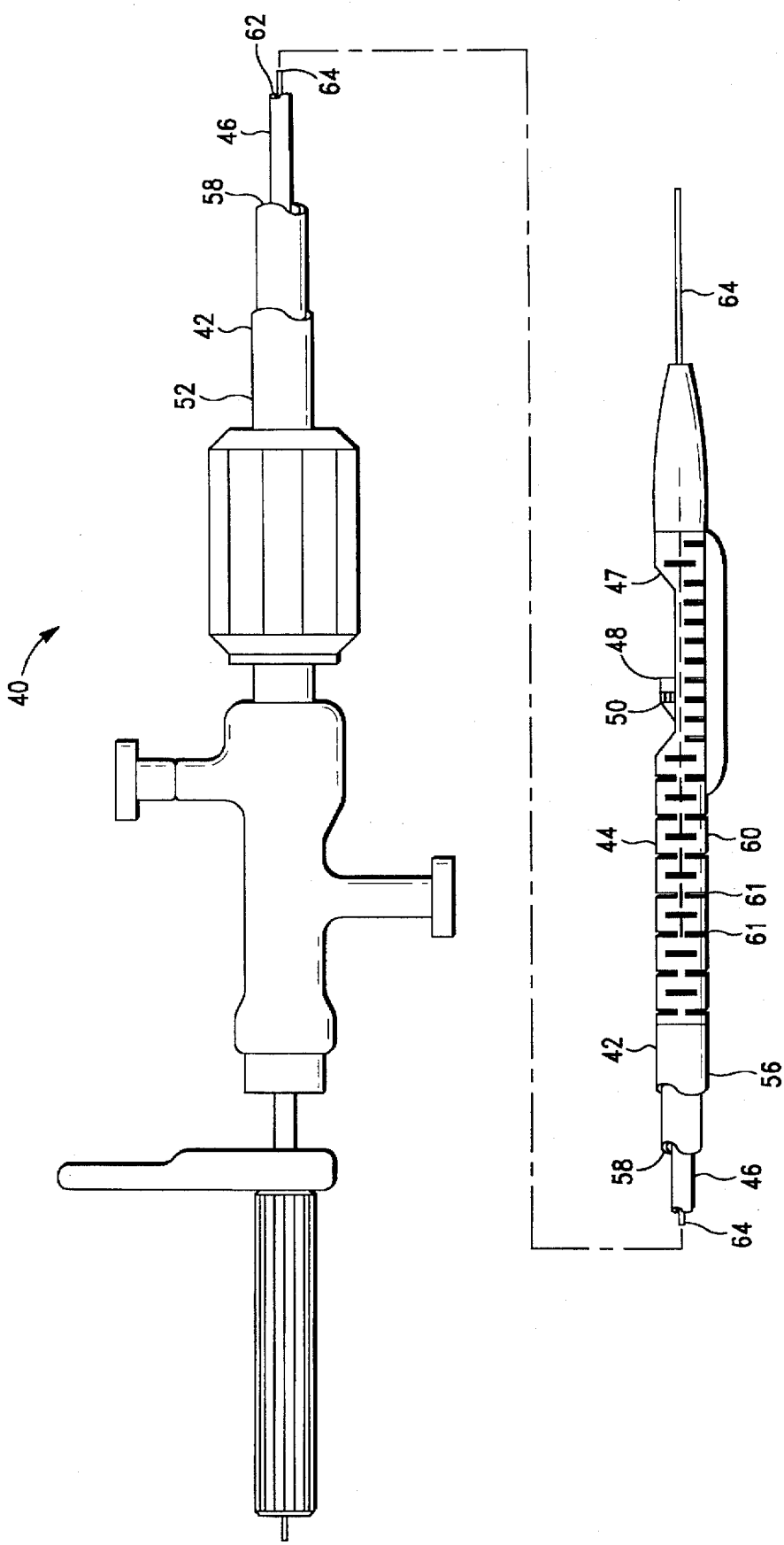
FIG. 1 is a orthographic view of a catheter device in accordance with the present invention.

The present invention will be described with reference to FIG. 1, which shows a catheter device in accordance with the present invention generally designated with the reference numeral 40. The catheter device 40 includes a catheter body 42, a housing 44, a torque cable 46, a work element 48 and a connector 50. The connector 50 interconnects the torque cable 46 with the work element 48 to facilitate flexion between the torque cable 46 and the work element 48.

The catheter body 42 has a proximal end 52 and a distal end 56. The catheter body 42 defines a torque cable lumen 58 which extends between the proximal end 52 and the distal end 56. The housing 44 attaches to the distal end 56 of the catheter body 42. The housing 44 houses the work element 48 and the connector 50. The torque cable 46 extends through the torque cable lumen 58 to the connector 50 in the housing 44. The work element 48 attaches to the torque cable 46 via the connector 50. The work element 48 may be adapted for purposes including imaging, cutting, delivering medication or otherwise interacting with tissue within a biological conduit.

The housing 44 defines a hollow flex tube 60 having multiple slots 61 to facilitate bending. The slots 61 are defined circumferentially about the flex tube 60. It can be appreciated that the slots 61 facilitate bending of the flex tube 60 while maintaining a desired degree of axial and torsional stiffness.

The flex tube 60 is fabricated from a flexible material such 304 stainless steel. The housing 44 has an interior 47. The interior 47 guides the work element 48 along the interior 47 of the housing 44. The interior 47 of the housing 44 is coated with titanium nitride to harden the interior 47 and inhibit interference between the work element 48 and the housing 44 when the housing 44 guides the work element 48. An example of a housing having a flex tube is disclosed in U.S. Pat. No. 5,226,909 the disclosure of which is incorporated by reference.

The torque cable 46 is fabricated from braided metal which bends and transmits torque. The torque cable 46 is hollow and defines an axial guidewire lumen 62. The guidewire lumen 62 receives a guidewire 64. The guidewire 64 slides within the guidewire lumen 62 for guiding the catheter device 40. An example of a torque cable is described in commonly assigned U.S. patent application Ser. No. 08/606,678, filed Feb. 26, 1996 entitled "Flexible composite Drive Shaft for Transmitting Torque" by Milo, et al., Attorney Docket No. DEVI1434CON, which is a file wrapper continuation of U.S. patent application Ser. No. 08/165,068, filed Dec. 9, 1993, entitled "composite Drive Shaft" by Milo, et al. and in U.S. Pat. No. 5,108,411, the disclosures of which are incorporated herein by reference.

With particular reference to FIG. 2 there is shown an embodiment of the catheter device 40. The distal end 56 of the catheter device 40 is operably positioned in a biological conduit 59. The biological conduit 59 is a blood vessel which contains stenotic material 63. The work element 48 includes a cutter 66. The cutter 66 has an arcuate cutting edge 68. The housing 44 includes a window 70. The window 70 exposes a portion of the cutter 66 and the cutting edge 68.

Accordingly, the catheter device 40 is particularly adapted for performing an atherectomy. Examples of typical atherectomy catheters with cutters are described in U.S. Pat. Nos. 5,250,059 and 5,071,425, the disclosures which are incorporated herein by reference. Examples of atherectomy catheters with helical cutters are described in U.S. Pat. Nos. 5,226,909 and 5,242,460, the disclosures of which are all incorporated herein by reference. It can be appreciated, however, that a myriad of work elements and various cutter types can be employed in accordance with the present invention.

The torque cable 46 rotates (e.g. rotationally oscillates) the cutter 66 and reciprocally slides the cutter 66 within the housing 44. The window 70 invaginates the stenotic material 63. The cutter 66 severs and removes portions of the stenotic material 63 when the cutter 66 rotates and slides past the window 70.

The biological conduit 59 is curved, having a bend as shown in FIG. 2. The housing 44 flexes to conform to the curved shape of the biological conduit 59. When the housing 44 flexes, the torque cable 46 bends slightly. The connector 50 bends in cooperation with the torque cable 46 to align the work element 48 coaxially with the housing 44 when the housing 44 flexes. Flexion of the connector 50 aligns the work element 48 with the housing 44 to maintain the work element 48 in coaxial alignment within the housing 44. Flexion of the connector 50 inhibits interference between the housing 44 and the work element 48 when the work element 48 rotates and slides in the housing 44.

The work element 48 includes, in a preferred embodiment, a sensor 54 such as an imaging device for sensing the interior of the biological conduit 59 and communicating with an imaging system. Examples of imaging systems and sensors used with catheters are described in U.S. Pat. Nos. 4,794,931 and 5,024,234 which are incorporated herein by reference. Although catheter devices 40 having work elements 48 which include imaging devices and cutters have been disclosed herein, it can be appreciated that there are a myriad of other work elements 48 which can be used in accordance with the present invention.

With reference to FIGS. 3 and 4, there is shown a cutter generally designated with the reference numeral 66. The cutter 66 defines a portion of the guide wire lumen 62. The cutter 66 has an arcuate cutting edge 68. The arcuate cutting edge 68 of the cutter 66 is sharp, having a thickness "t" of approximately 5–10 microns. The cutting edge 68 is fabricated from a hard metal to maintain the sharpness of the cutting edge 68. In one embodiment, the cutting edge 68 is made from tungsten carbide. In one embodiment, the cutting edge 68 is coated with titanium nitride to harden the cutting edge 68.

With particular reference to FIG. 3, there is shown the cutter 66. The cutter 66 has an outer periphery having a uniform radius $r_1$. The cutting edge has a uniform radius $r_2$ which is within 5 microns smaller than the uniform radius $r_1$.

With particular reference to FIG. 4, there is shown the cutter 66. The cutter 66 has an outer periphery with a uniform radius $r_1$. The cutter 66 has a beveled portion external to the cutter 66. The beveled portion is defined at one end of the cutter 66 to form a sharp cutting edge 68. The beveled portion of the cutter 66 has a length l. The length l is within the range of 0.0005 and 0.0015 inches long. The cutting edge 68 has a radius of curvature of between 0.00035–0.00055 inches smaller than the uniform radius $r_1$ of the outer periphery of the cutter.

The beveling of the cutter 66 facilitates sliding of the cutter 66 within the housing 44 when the housing 44 flexes. The arcuate cutting edge 68 is defined on the beveled portion of the cutter 66.

Figures 5, 6:
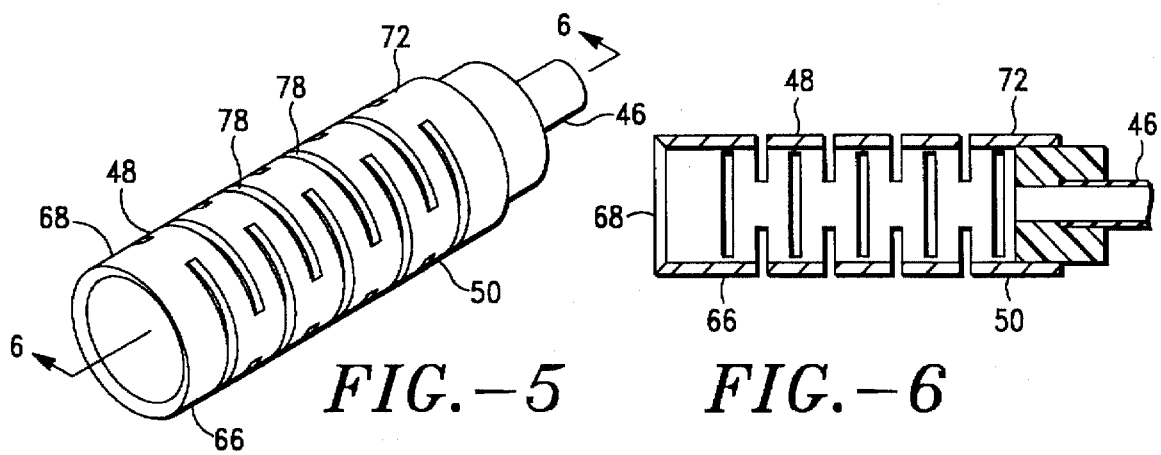
FIG. 5 is a perspective view of a connector in accordance with the present invention.
FIG. 6 is a cross-sectional view of the connector of FIG. 5 as seen along the line 6—6 in the direction of the arrows.

With particular reference to FIG. 5, there is shown an embodiment of the present invention having a work element 48 formed integrally with the connector 50. The connector 50 includes a flex tube 72 having two ends. The work element 48 includes a cutter 66 which is defined on one end of the flex tube 72. The other end of the flex tube 72 attaches to the torque cable 46.

The flex tube 72 is fabricated from a flexible metal and has a plurality of circumferential slots 78. Each slot 78 partially circumscribes the flex tube 72. In one embodiment, the flex tube 72 is fabricated from 304 grade stainless steel.

With particular reference to FIG. 6, there is shown the connection between the connector 50 and the torque cable 46 of FIG. 5. The torque cable 46 attaches to the connector 50 with a pressed fit. The torque cable 46 also bonds to the connector 50 via bonding techniques such as adhesive bonding, soldering, welding, etc.

Figures 7, 8:
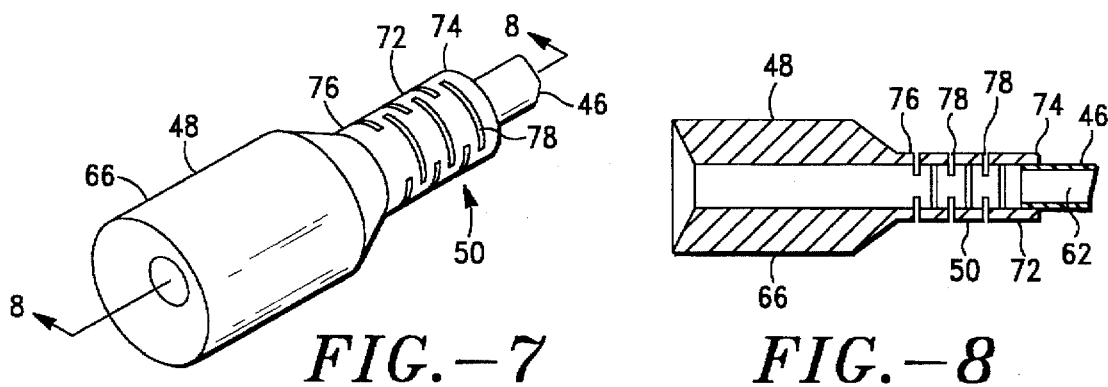
FIG. 7 is a perspective view of a connector in accordance with the present invention.
FIG. 8 is a cross-sectional view of a connector of FIG. 7 as seen along the line 8—8 in the direction of the arrows.

With particular reference to FIG. 7, there is shown the work element 48 connected with the connector 50. The connector 50 has a proximal end 74 and a distal end 76. The proximal end 74 of the connector 50 attaches to the torque cable 46. The distal end 76 of the connector 50 attaches to the work element 48.

The connector 50 includes a flex tube 72 having multiple circumferential slots 78 to facilitate flexion of the connector 50. The slots 78 permit bending while maintaining axial and torsional stiffness of the connector 50.

With particular reference to FIG. 8, there is shown the connector 50 and the work element 48 of FIG. 7. The connector 50 abuts the work element 48 and attaches to the work element 48 by an appropriate technique such as welding, brazing, soldering and adhesive bonding. The torque cable 46, the connector 50 and the work element 48 are hollow to define a guidewire lumen 62.

Figure 9:
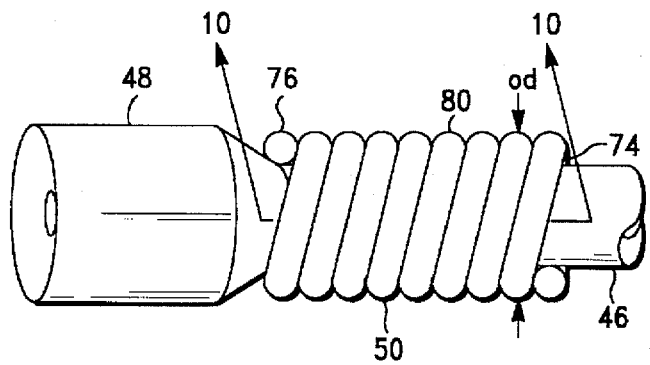
FIG. 9 is a perspective view of a connector in accordance with the present invention.

With particular reference to FIG. 9, there is shown the work element 48, the connector 50 and the torque cable 46. The connector 50 includes a helical spring 80 which winds continuously from the torque cable 46 to the work element 48. The helical spring 80 attaches to the torque cable 46 and to the work element 48 at the proximal end 74 and the distal end 76 respectively by a method such as soldering, welding, and adhesive bonding.

It can be appreciated that rotation of the torque cable 46 will wind the spring 80 to grip and rotate the work element 48.

Figure 10:
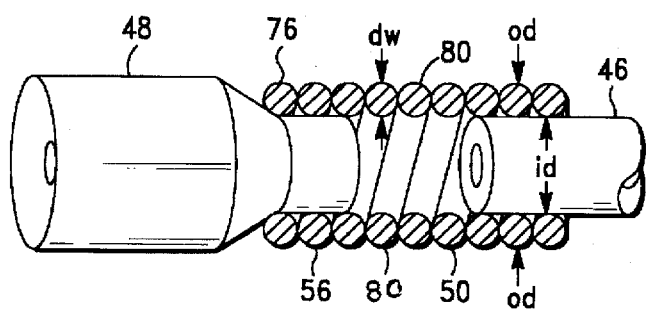
FIG. 10 is a cutaway view of a connector in of FIG. 9 as seen along the line 10—10 in the direction of the arrows.

With particular reference to FIG. 10, there is shown the helical spring 80 which is fabricated from a single wire. The wire has a diameter $d_w$ within the range of 0.012 inches to 0.017 inches. The torque cable 46 rotates in a single direction. The wire is wound in a single direction which coincides with the rotational direction of the torque cable 46. The helical spring 80 has an inside diameter (id) of about 0.037 inches (FIG. 10) and an outside diameter (od) of less than 0.073 inches.

Figure 11:
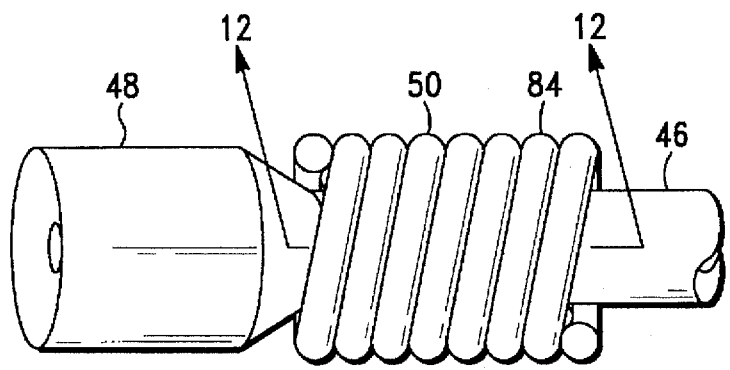
FIG. 11 is a perspective view of a connector in accordance with the present invention.

With particular reference to FIG. 11, there is shown the work element 48, the connector 50 and the torque cable 46. The torque cable 46 rotates the connector 50 and the work element 48. The connector 50 circumscribes both the torque cable 46 and the work element 48.

Figure 12:
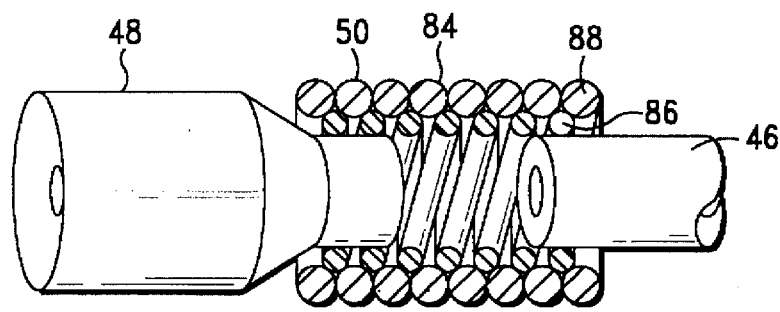
FIG. 12 is a cutaway view of the connector of FIG. 11 as seen along the line 12—12 in the direction of the arrows.

With particular reference to FIG. 12, there is shown an embodiment of the connector 50 of FIG. 11. The connector 50 includes a duplex style spring 84. The duplex style spring 84 includes a helical spring 86 and a helical spring 88. The spring 86 winds internal to the spring 88 in a direction opposing the spring 88. Spring 88 winds external to spring 86. The springs 86 and 88 cooperate compositely to transmit torque from the torque cable 46 to the work element 48.

When the torque cable 46 rotates, the internally wound spring 86 expands against the externally wound spring 88. The externally wound spring 88 simultaneously contracts towards the internally wound spring 86. When the torque cable 46 rotates, the oppositely wound springs 86 and 88 provide increased axial and torsional rigidity to the connector 50.

Figure 13:
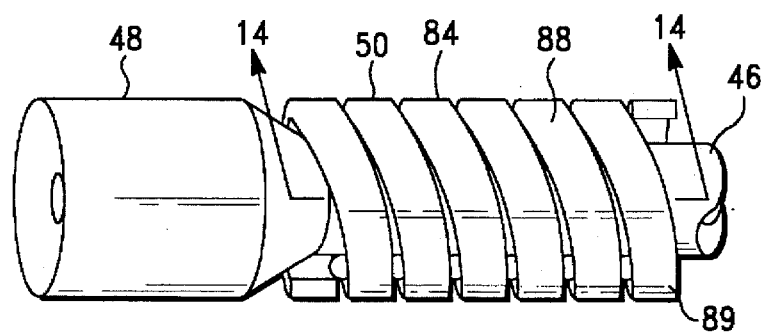
FIG. 13 is a perspective view of a connector in accordance with the present invention.

With particular reference to FIG. 13, there is shown an embodiment of the connector 50. The connector 50 includes a duplex style spring 84. The duplex style spring includes a flat outer surface 89.

Figure 14:
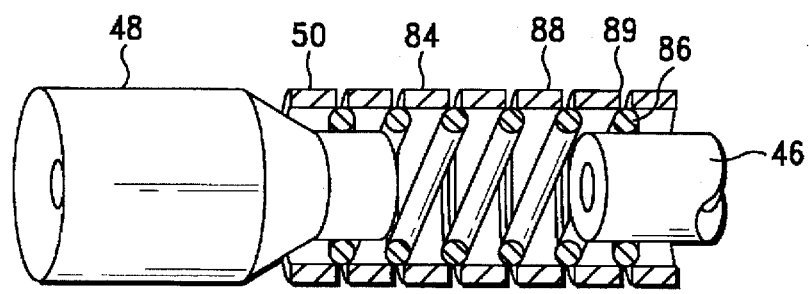
FIG. 14 is a partial cross-sectional view of the connector of FIG. 13 as seen along the line 14—14 in the direction of the arrows.

With particular reference to FIG. 14, there is shown the connector 50 of FIG. 13. The duplex style spring 84 includes a helical spring 86 and a helical spring 88. Spring 86 winds internal to the spring 88. The spring 88 has a rectangular cross-section and a flat and smooth outer surface 89. The shape and size of the spring 86 and the spring 88 in conjunction with the number of coils per inch, and material qualities such as the spring constant are characteristics which are variable and can be varied as a matter of design until optimal bending, torsion and axial strains are achieved under desired loading.

Figure 15:
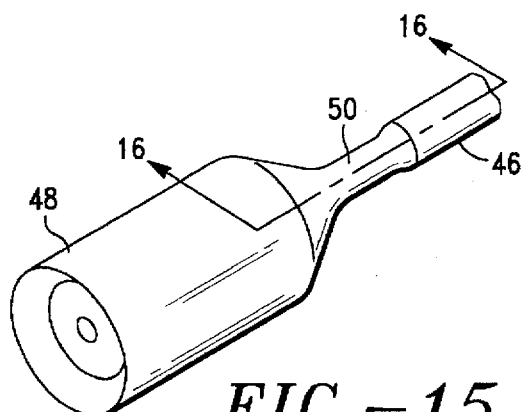
FIG. 15 is a perspective view of a connector in accordance with the present invention.

With particular reference to FIG. 15, there is shown an embodiment of the connector 50. The connector 50 is formed integrally with the torque cable 46. The connector 50 has a geometry which varies from the geometry of the torque cable 46 and which causes the connector 50 to achieve a higher degree of flexion than the torque cable 46 has.

Figure 16:
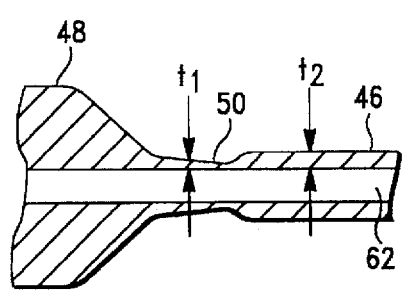
FIG. 16 is a cross-sectional view of the connector of FIG. 15 as seen along the line 16—16 in the direction of the arrows.

With particular reference to FIG. 16, there is shown the connector 50 of FIG. 15. More particularly, the connector 50 and the torque cable 46 each have a wall thickness $t_1$ and $t_2$ respectively. The wall thickness $t_1$ of the connector 50 is relatively less than the wall thickness $t_2$ of the torque cable 46 to cause the connector 50 to be relatively more flexible than the torque cable 46.

It can be appreciated that the geometry of the connector can assume a variety of configurations which provide a higher degree of flexion to the connector 50 than the geometry of the torque cable 46 can.

Figure 17:
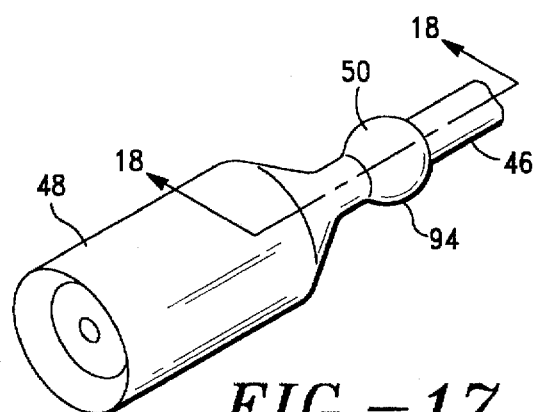
FIG. 17 is a perspective view of a connector in accordance with the present invention.

With particular reference to FIG. 17, there is shown an embodiment of the connector 50. The connector 50 is formed within the torque cable 46 and is identifiable by a circular shaped ball 94. The ball 94 causes a higher degree of flexion in the connector 50 than the torque cable 46 has.

Figure 18:
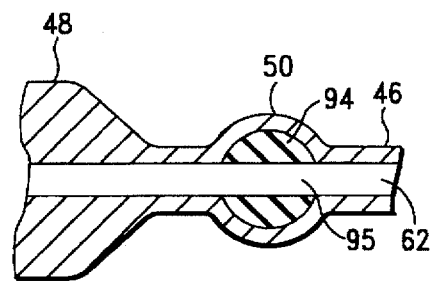
FIG. 18 is a cross-sectional view of the connector of FIG. 17 as seen along the line 18—18 in the direction of the arrows.

With particular reference to FIG. 18, there is shown the connector 50 of FIG. 17. The ball 94 is held within the torque cable 46. The ball 94 deforms the geometry of the torque cable 46 to facilitate bending of the connector 50. The ball 94 has a hole 95 which aligns with the torque cable 46 to define a portion of the guidewire lumen 62 and to accommodate a guidewire.

Figure 19:
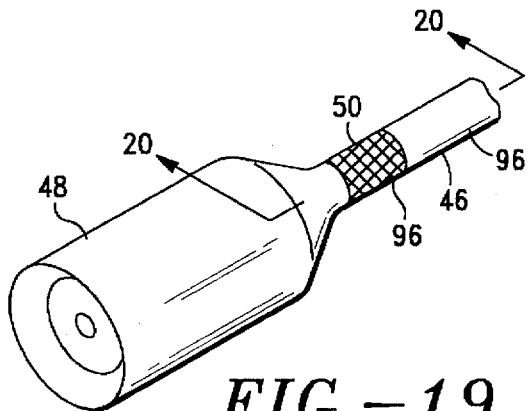
FIG. 19 is a perspective view of a connector in accordance with the present invention.

With particular reference to FIG. 19, there is shown an embodiment of the connector 50. The connector 50 is formed integrally with the torque cable 46. The connector 50 is formed of a resilient material. The torque cable 46 is cylindrical in shape having a diameter. The connector 50 has a diameter which coincides with the diameter of the torque cable 46.

Figure 20:
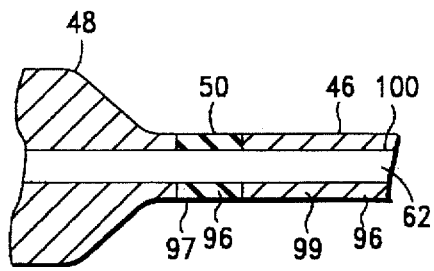
FIG. 20 is a cross-sectional view of the connector of FIG. 19 as seen along the line 20—20 in the direction of the arrows.

With particular reference to FIG. 20, there is shown the connector 50 of FIG. 19. The torque cable 46 and the connector 50 are extruded from a fiber reinforcement 96.

The fiber reinforcement includes a matrix 97. In one embodiment, the matrix 97 is formed from thermoplastic copolymer.

The fiber reinforcement 96 includes a stainless steel braid. The matrix 97 includes a low durometer (soft) polymer. Low durometer polymers include pebax and thermoset urethane. The matrix 97 defines the connector 50. The remainder of the torque cable 46 includes a matrix 99 having a relatively higher durometer polymer than the matrix 97. The matrix 97 causes the connector 50 to achieve a higher degree of flexion than the matrix 97 of the torque cable 46 does. Accordingly, the connector 50 bends more readily than the torque cable 46.

In one embodiment, the matrix 97 of the connector 50 is impregnated with a third material to facilitate a higher degree of flexion and increased bending. Although various ways of facilitating flexion of the connector 50 to permit the connector 50 to bend are disclosed, it can be appreciated that the connector 50 can include various material combinations which will facilitate flexion and reduce the bending forces transmitted by the connector 50.

Figure 21:
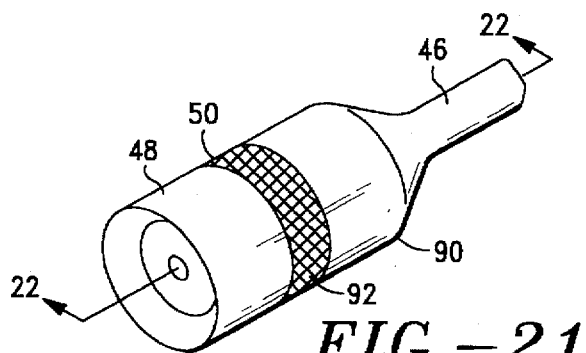
FIG. 21 is a perspective view of a connector in accordance with the present invention.

With particular reference FIG. 21, there is shown an embodiment of the connector 50. The connector 50 includes a resilient member 92, and a bushing 90. The bushing 90 attaches to the torque cable 46. The resilient member 92 attaches the work element 48 to the bushing 90.

The bushing 90 transmits torsional, bending and axial forces between the torque cable 46 and the resilient member 92. The resilient member 92 transmits torsional and axial forces between the torque cable 46 to the work element 48. The resilient member 92 bends with respect to the bushing 90 in response to bending forces and thereby inhibits the transmission of bending forces between the torque cable 46 and the work element 48 through the resilient member 92.

Figure 22:
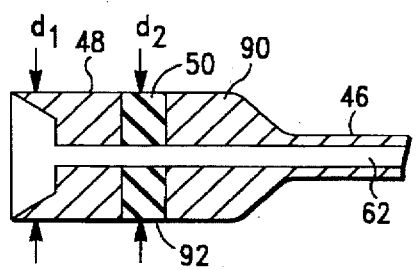
FIG. 22 is a cross-sectional view of the connector of FIG. 21 as seen along the line 22—22 in the direction of the arrows.

With particular reference to FIG. 22, there is shown the connector 50 of FIG. 21. The work element 48 has a diameter $d_1$. The connector 50 has a diameter $d_2$. The diameter $d_1$ of the work element 48 coincides with the diameter $d_2$ of the connector 50.

The bushing 90, the work element 48 and the resilient member 92 are hollow to define a portion of the guidewire lumen 62.

Figure 23:
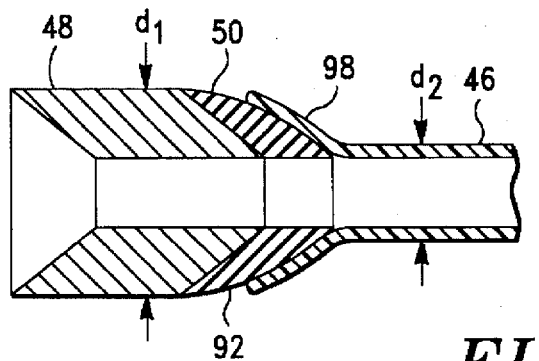
FIG. 23 is a cross-sectional view of a connector in accordance with the present invention.

With particular reference to FIG. 23, there is shown the work element 48, the connector 50 having the resilient member 92, and the torque cable 46. The work element has a diameter $d_1$. The torque cable has a diameter $d_2$ which is relatively smaller than the diameter of the work element. The resilient member 92 is tapered at a variable slope from the work element 48 to the torque cable 46. The torque cable 46 has a sleeve 98 which partially covers the resilient member 92 and conforms to the variable slope of the resilient member.

Figure 24:
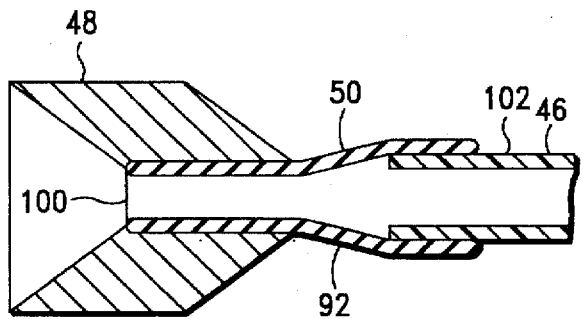
FIG. 24 is a cross-sectional view of a connector in accordance with the present invention.

With particular reference to FIG. 24, there is shown the work element 48, the torque cable 46, and the connector 50. The connector 50 includes the resilient member 92. The work element 48 has an interior 100. The torque cable 46 has an exterior 102.

The resilient member 92 attaches between the interior 100 of the work element 48 and the exterior 102 of the torque cable 46. Attachment of the resilient member 92 between the work element 48 and the torque cable 46 is accomplished by adhesive bonding.

Figure 25:
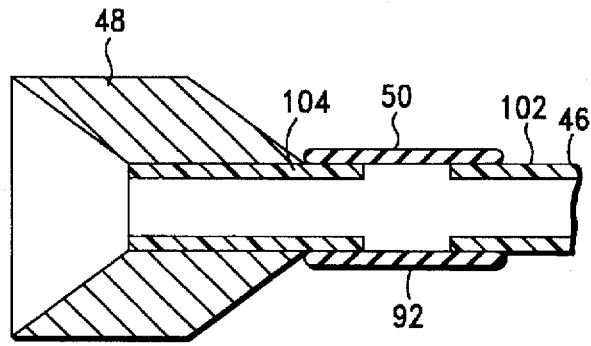
FIG. 25 is a cross-sectional view of a connector in accordance with the present invention.

With particular reference to FIG. 25, there is shown the torque cable 46, the work element 48 and the connector 50. The connector 50 includes the resilient member 92. The work element 48 has an internal annular extension 104. The torque cable 46 has an exterior 102.

The resilient member 92 attaches between the annular extension 104 of the work element 48 and the exterior 102 of the torque cable 46. The respective diameters of the work element 48, the connector 50, and the torque cable 46 are sized so that the diameter of the work element 48 is the largest and the diameter of the torque cable 46 is the smallest.

Figure 26:
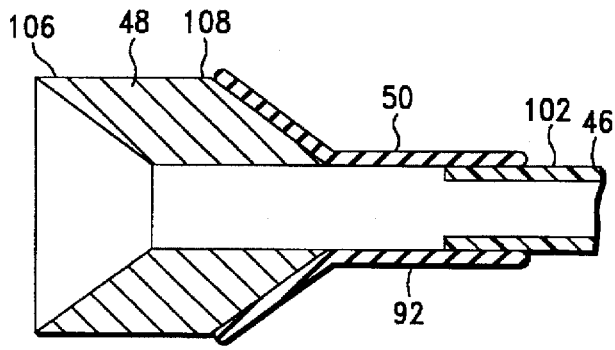
FIG. 26 is a cross-sectional view of a connector in accordance with the present invention.

With particular reference to FIG. 26, there is shown an embodiment of the torque cable 46, the work element 48 and the connector 50. The connector 50 includes the resilient member 92. The work element 48 has a distal end 106 and a proximal end 108. The proximal end 108 is tapered. The torque cable 46 has an exterior 102. The resilient member 92 has a flared end which attaches to the proximal end 108 of the work element 48, and another end which attaches to the exterior 102 of the torque cable 46.

Figure 27:
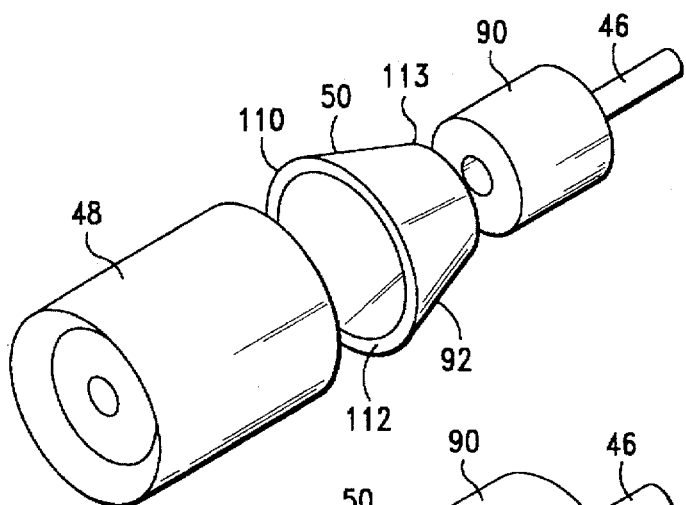
FIG. 27 is an exploded perspective view of a connector in accordance with the present invention.

With particular reference to FIG. 27, there is shown an embodiment of the work element 48, the connector 50, the bushing 90 and the torque cable 46. The connector 50 includes a resilient and deformable wobble plate 110 having annular ends 112 and 113 connectable with the work element 48 and the bushing 90 respectively. The wobble plate 110 is generally conical in shape having a hollow interior and two open ends. The annular end 112 connects with the work element 48. The annular end 113 connects with the bushing 90. The bushing 90 is relatively smaller in diameter than the work element 48. The wobble plate 110 facilitates interconnection of various bushings and work elements of different diameters.

Figure 28:
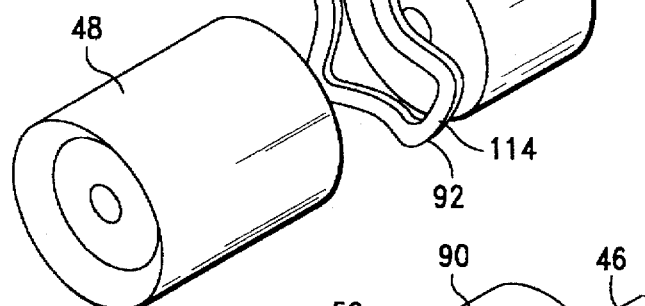
FIG. 28 is an exploded perspective view of a connector in accordance with the present invention.

With particular reference to FIG. 28, there is shown an embodiment of the work element 48, the connector 50, and the torque cable 46. The connector 50 includes a resilient member 92. The resilient member is an annular spring 114. The spring 114 is normally wavy. The spring 114 is compressible between a wavy configuration to a flat configuration. The spring 114 partially compresses between the work element 48 and the bushing 90 to permit the connector 50 to flex.

Figure 29:
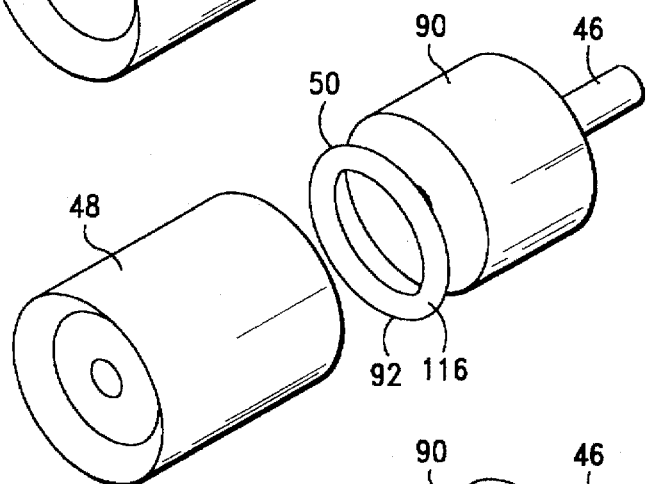
FIG. 29 is an exploded perspective view of a connector in accordance with the present invention.

With particular reference to FIG. 29, there is shown the work element 48, the bushing 90, the torque cable 46 and the connector 50. The connector 50 is resilient and includes an o-ring 116. The work element 48 and the bushing 90 compress the o-ring 116. The o-ring 116 facilitates bending between the work element 48 and the bushing 90.

Figure 30:
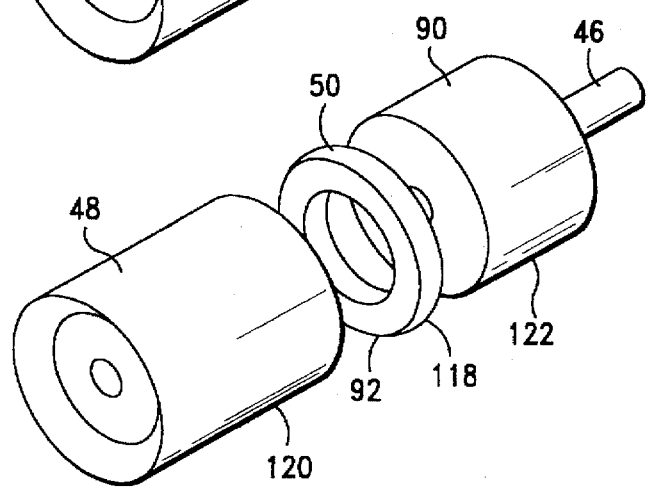
FIG. 30 is an exploded perspective view of a connector in accordance with the present invention.

With particular reference to FIG. 30, there is shown an embodiment of the work element 48, the connector 50, a bushing 90, and the torque cable 46. The connector 50 is cylindrical and formed with a hollow center and an outer surface 118. The work element 48 and the bushing 90 have outer surfaces 120 and 122 respectively. The outer surfaces 118, 120 and 122 lie co-radially. The connector 50 is resilient, being fabricated from an elastomeric material.

Figures 31, 32:
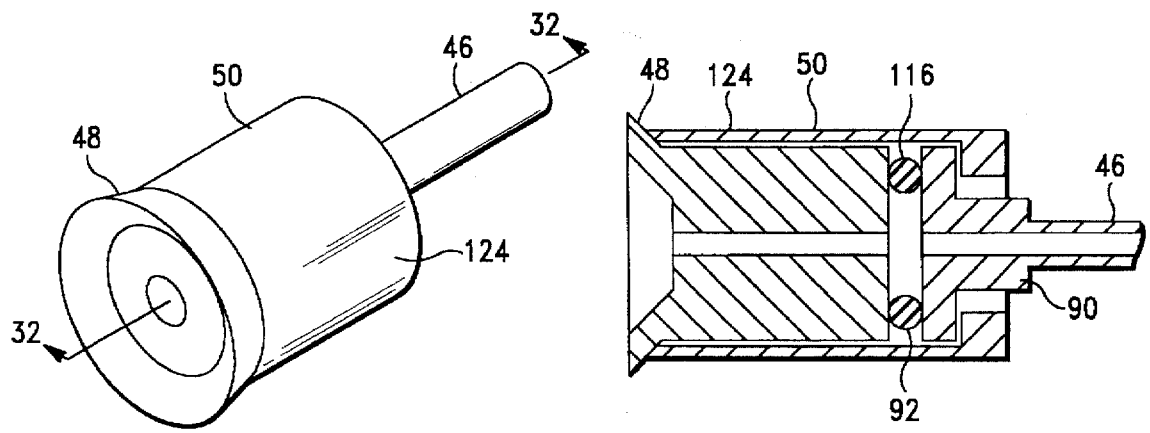
FIG. 31 is a perspective view of a connector in accordance with the present invention.
FIG. 32 is a cross-sectional view of the connector of FIG. 31 as seen along the line 32—32 in the direction of the arrows.

With particular reference to FIG. 31, there is shown an embodiment of the connector 50. The connector 50 includes a locking sleeve 124. The locking sleeve 124 attaches to the work element 48 by an appropriate method such as a snap fit, threaded engagement, or adhesive bonding. The locking sleeve 124 circumscribes a portion of the work element 48 to hold the work element 48 with the torque cable 46.

With particular reference to FIG. 32, there is shown the connector 50 of FIG. 31. The connector 50 includes a bushing 90, and an o-ring 116. The bushing 90 and the work element 48 compress the o-ring 116 therebetween. The locking sleeve 124 circumscribes the o-ring 116 and the bushing 90 to normally hold the bushing 90, the o-ring 116 and the work element 48 in axial alignment. The locking sleeve 124 mechanically locks about the bushing 90 to permit movement of the bushing with respect to the locking sleeve 124. The locking sleeve 124 engages an annular periphery of the bushing 90 to transmit torque and axial forces from the torque cable 46 via the bushing 90 to the work element 48 in response to rotation of the torque cable 46.

The locking sleeve 124 flexes to facilitate the bushing 90 to bend with respect to the work element 48. The o-ring 116 and the locking sleeve 124 cooperate and flex together to facilitate flexion of the connector 50 and thereby reduce the magnitude of bending forces transmitted between the work element 48 and the torque cable 46.

Figure 33:
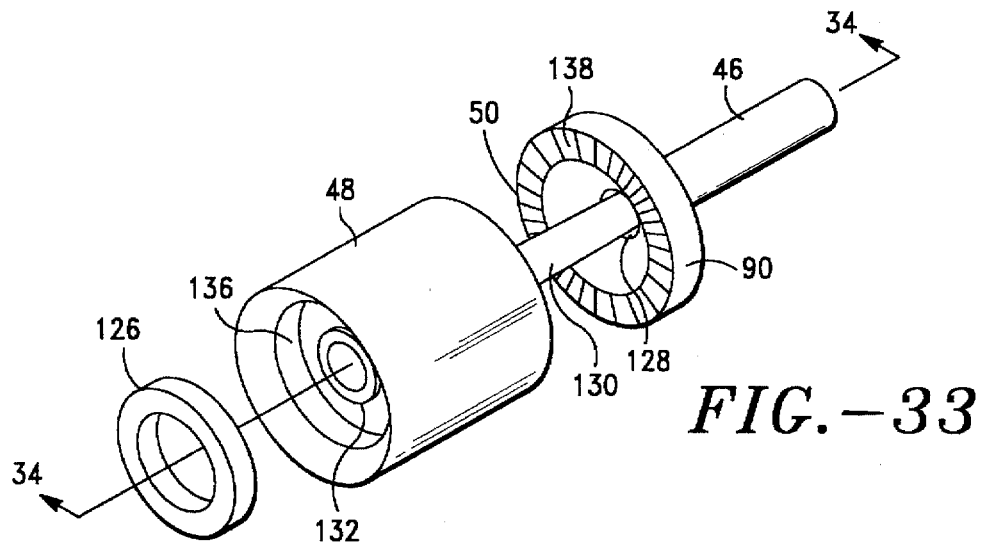
FIG. 33 is an exploded perspective view of a connector in accordance with the present invention.

With particular reference to FIG. 33, there is shown the work element 48, the connector 50 and a cap 126. The connector 50 includes a bushing 90 and an internal sleeve 130. The internal sleeve has a proximal end 128 and a distal end 132. The bushing has a clutch plate surface 138. The work element 48 has an annular groove 136. The cap 126 attaches the distal end 132 of the internal sleeve 130 in the annular groove 136.

The internal sleeve 130 is flexible. The proximal end 128 of the internal sleeve 130 attaches to the torque cable 46. The distal end 132 attaches to the work element 48 in the annular groove 136. The cap 126 inserts into the annular groove 136 to hold the distal end 132 of the internal sleeve 130. The bushing 90 circumscribes the proximal end 128 of the internal sleeve 130.

Figure 34:
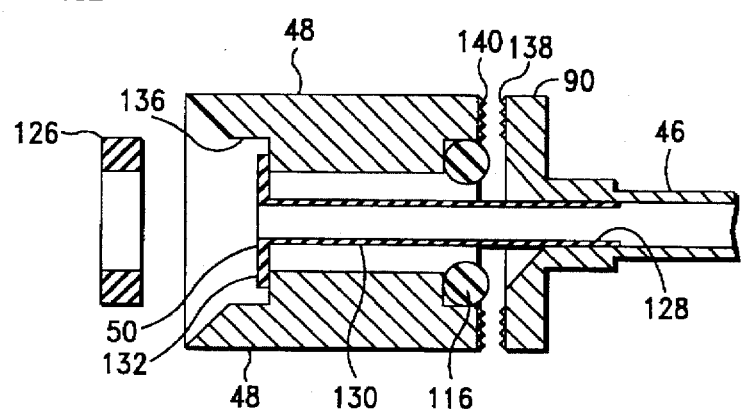
FIG. 34 is a cross-sectional view of the connector of FIG. 31 as seen along the line 33—33 in the direction of the arrows.

With particular reference to FIG. 34, there is shown the work element 48, the connector 50 and the cap 126 of FIG. 33. The clutch plate surface 138 is defined on one end of the bushing 90. A clutch plate surface 140 is defined on one end of the work element 48. The clutch plate surface 138 of the bushing 90 aligns with and engages the clutch plate surface 140 of the work element to transmit torque between the bushing 90 and the work element 48.

An o-ring 116 attaches between the bushing 90 and the work element 48 to normally bias the clutch plate surfaces 138 and 140 apart. The connector 50 draws the clutch plate surfaces 138 and 140 together. The clutch plate surfaces 138 and 140 transmit torque between the bushing 90 and the work element. For the purposes herein, a clutch plate surface includes coupling mechanisms which interconnect drive and driven mechanisms to transmit torque.

With particular reference to FIG. 35, there is shown an embodiment of the work element 48, the connector 50, and the torque cable 46. The connector 50 includes a bushing 90 and a rigid internal sleeve 130 having proximal end 128 and a distal end 132. The internal sleeve 130 is rigid. The work element 48 includes a clutch plate surface 140. The bushing 90 includes a clutch plate surface 138.

The work element 48 slidably attaches to the connector 50 in the direction of the arrows which are shown above the work element 48. The work element 48 slides from a position where the work element 48 engages the distal end 132 of the internal sleeve 130 as shown, to a position where the clutch plate surfaces 138 and 140 contact.

The bushing 90 and the work element 48 engage to selectively transmit torque between the bushing 90 and the work element 48 when the torque cable 46 urges the bushing 90 and the work element 48 together.

The work element 48 defines a space 142 between the connector 50 and the work element 48. The space 142 permits the work element 48 to flexibly connect with the bushing 90. The connector 50 aligns the work element 48 and the bushing 90 to permit the clutch plate surfaces 138 and 140 to contact and transmit torque such as when the torque cable 46 slides axially towards the distal end 132 of the connector 50.

With particular reference to FIGS. 36 and 37 there is shown an embodiment of the work element 48, the connector 50, and the torque cable 46. The work element 48 has an annular lock 152 and a geared portion 144. The connector 50 includes a pinion 146. The pinion 146 has arcuate gear teeth 148. The arcuate gear teeth 148 are helical in shape and mesh with the geared portion 144 of the work element 48 to transmit torque at a variable angle.

The annular lock 152 inserts into the work element 48 to axially hold the pinion 146. The pinion 146 meshes with the geared portion 144 at a variable angle to transmit torque.

It can be appreciated that although the pinion 146 meshes with the geared portion 144, other ways of transmitting torque through a connector can be used in accordance with the present invention. For example, the connector 50 can include a keyway and the work element 48 can include a keyway. A key can insert between each keyway to transmit torque between the connector 50 and the work element 48 at a variable angle.

With particular reference to FIG. 38 there is shown an embodiment of the work element 48, the connector 50, and the torque cable 46. The connector 50 includes a universal joint 150. The universal joint 150 attaches to the work element 48 and to the torque cable 46. The universal joint 150 facilitates the bending of the work element 48 with respect to the connector 50 in a plane about the axis 154. The universal joint 150 has a bushing 90 which attaches the torque cable 46 to the universal joint 150. The bushing 90 bends with respect to the universal joint in a plane about the axis 156.

While the foregoing detailed description describes various embodiments of the catheter device 40 in accordance with the present invention, it is to be understood that the above description is illustrative by example only and not limiting of the disclosed invention. It will be appreciated that the specific type of connector 50 used can differ from the examples shown in the accompanying figures and remain within the scope and spirit of this invention. The invention is to be limited only by the claims set forth below.

We claim:

1. A catheter device insertable into a biological conduit, comprising:

a catheter body having a proximal end and a distal end, the catheter body defining a torque cable lumen extending between the proximal end and the distal end;

a housing connected to the distal end of the catheter body, the housing being flexible and defining an opening;

a torque cable extending between the proximal end and the distal end of the catheter body through the torque cable lumen, the torque cable being capable of sliding with respect to the torque cable lumen;

a work element slidably disposed within the housing; and a connector interconnecting the work element and the torque cable, the connector being flexible and including a flex tube, the flex tube having multiple radial slots to facilitate flexion of the connector, the work element being formed unitary with the connector, whereby when the housing flexes and the torque cable slides the work element, the connector flexes and the housing guides the work element within the housing.

2. A catheter device insertable into a biological conduit, comprising:

a catheter body having a proximal end and a distal end, the catheter body defining a torque cable lumen extending between the proximal end and the distal end;

a housing connected to the distal end of the catheter body, the housing being flexible and defining an opening;

a torque cable extending between the proximal end and the distal end of the catheter body through the torque cable lumen, the torque cable being capable of sliding with respect to the torque cable lumen;

a work element slidably disposed within the housing; and a flexible connector interconnecting the work element and the torque cable, the connector including a flex tube having multiple radial slots to facilitate flexion of the connector, the flex tube having two ends, the work element being formed integral with the connector and having an arcuate cutting edge defined by one end of the flex tube, the other end of the flex tube being attached to the torque cable, whereby when the housing flexes and the torque cable slides the work element, the connector flexes and the housing guides the work element within the housing.

3. A catheter device insertable into a biological conduit, comprising:

a catheter body having a proximal end and a distal end, the catheter body defining a torque cable lumen extending between the proximal end and the distal end;

a housing with a longitudinal axis connected to the distal end of the catheter body, the housing is flexible and defines an opening, the housing flexes when inserted into a biological conduit;

a torque cable extending between the proximal end of the catheter body through the torque cable lumen towards the distal end, the torque cable defining a portion of a guidewire lumen;

a work element disposed within the housing, the work element defining a portion of the guidewire lumen; and a connector attached to the work element and to the torque cable, the connector being bendable with the longitudinal axis of the housing, the connector defining a portion of the guidewire lumen, the connector being rotationally rigid to transmit torque from the torque cable via the connector to the work element and transmitting said torque while not rotationally deforming, the connector being axially rigid to maintain a constant length in response to axial forces transmitted from the torque cable via the connector to the work element, whereby when the housing flexes and the torque cable moves to actuate the work element within the housing, the connector bends and the housing retains the work element.

* * * * *